United States Patent [19]

Ishimatsu et al.

[11] 4,205,128
[45] May 27, 1980

[54] PROCESS FOR PRODUCING IMMOBILIZED ENZYME COMPOSITIONS

[75] Inventors: Yoshiaki Ishimatsu, Machida; Shigeki Shigesada, Sagamihara; Hiroyasu Suzuki, Tokyo; Hironoshin Kitagawa; Shoji Kimura, both of Machida, all of Japan

[73] Assignee: Denki Kagaku Kogyo Kabushiki Kaisha, Tokyo, Japan

[21] Appl. No.: 936,773

[22] Filed: Aug. 25, 1978

Related U.S. Application Data

[63] Continuation of Ser. No. 781,921, Mar. 28, 1977, abandoned.

[30] Foreign Application Priority Data

Mar. 31, 1976 [JP] Japan ................................ 51/35471

[51] Int. Cl.$^2$ ............................................... C07G 7/02
[52] U.S. Cl. ........................................ 435/182; 435/94; 435/99; 435/205; 435/227; 435/234
[58] Field of Search .................. 195/63, 68, DIG. 11, 195/31 F, 59

[56] References Cited

U.S. PATENT DOCUMENTS

| Re. 29,130 | 2/1977 | Lee et al. | 195/31 F |
|---|---|---|---|
| 3,705,084 | 12/1972 | Reynolds | 195/63 |
| 3,838,007 | 9/1974 | Van Velzen | 195/63 X |
| 3,915,797 | 10/1975 | Ishimatsu et al. | 195/63 X |
| 3,980,521 | 9/1976 | Amotz et al. | 195/63 X |
| 4,001,264 | 1/1977 | Garidge et al. | 195/68 X |

*Primary Examiner*—David M. Naff
*Attorney, Agent, or Firm*—Oblon, Fisher, Spivak, McClelland & Maier

[57] ABSTRACT

Immobilized enzyme compositions for industrial use are produced by reacting an enzyme and/or enzyme-containing microorganism cells with an anion-exchange high molecular substance having a quaternary pyridine ring in the molecule, and then subjecting the reaction products to molding and drying in a molding machine. A polyfunctional crosslinking agent may be added at any stage of the process. The immobilized enzyme compositions thus prepared can be packed in a reactor of an industrial scale for continuous enzyme reaction.

13 Claims, No Drawings

PROCESS FOR PRODUCING IMMOBILIZED ENZYME COMPOSITIONS

This is a continuation of application Ser. No. 781,921, filed Mar. 28, 1977, now abandoned.

BACKGROUND OF THE INVENTION

1. Field of the Invention

This invention relates to a process for producing immobilized enzyme compositions useful for industrial applications.

2. Description of the Prior Art

Immobilization of enzymes is often very advantageous in industrial applications. One of the industrially important merits is that the immobilized enzymes can be packed in a column type reactor to serve for a continuous enzyme reaction over a long period of time.

Various techniques for the enzyme immobilization have thus far been proposed, particularly with regard to glucose isomerase which, in the immobilized state, has a great importance in industrial applications, for example, in U.S. Pat. No. 3,821,086 to Reynolds (issued June 28, 1975), U.S. patent application Ser. No. 501,292 now U.S. Pat. No. 3,980,521 by NOVO (filed Aug. 28, 1974) and U.S. Pat. No. 3,915,797 to Ishimatsu et al. (issued Oct. 28, 1975).

This invention contemplates to provide a further development over the prior art immobilization techniques, more particularly to provide a process for producing immobilized enzyme compositions of an excellent physical strength, with an outstandingly high enzymatic activity and a resonable stability and showing a sufficient liquid penetration when packed in a reactor of an industrial scale as compared with immobilized enzymes of the prior art.

This invention stems from our prior invention wherein an immobilized enzyme of a high enzymatic activity and an excellent stability can be produced by immobilizing an enzyme and/or enzyme-containing microorganic cells into an anion-exchange high molecular substance containing a quaternary pyridine ring in the molecule, that is, a reactive high polymer insoluble in water but hydrophilic obtained by quaternization of vinylpyridine copolymer, making an improvement in the physical strength of the immobilized enzyme which has been a serious drawback of the above invention.

The above improvement has been attained by the process comprising the steps of subjecting an enzyme and/or enzyme-containing microorganic cells, after reaction with the above described anion-exchange high polymer, to extrusion molding in an extruder under a predetermined humidity condition, pelletizing in a pelletizing machine if required, and then to drying under a certain temperature condition into immobilized enzyme pellets of a $100\mu - 2$ mm pellet size. The chemical reaction between the anion-exchange high polymer and the enzyme and/or enzyme-containing microorganic cells can be accelerated by the above drying treatment thus enabling the production of a catalyst of an excellent physical strength. In addition, pelletizing in the extrusion molding prior to the drying can significantly increase the drying efficiency to minimize the heat energy required for the chemical reaction thereby preventing the excess supply of the heat energy which may cause damages to the enzymatic activity.

Besides, a great pressure loss is often experienced with large-scaled industrial reactors or reactors using industrial materials of high density and viscosity such as for the hydrolysis and isomerization of dextrose, and therefore catalysts to be used therein should be strong enough to suppress such a pressure loss. The invention has succeeded in making a further development based on the above improvement by the addition of a bifunctional crosslinking agent capable of reacting with the anion-exchange high polymer or the enzyme described above.

While the above crosslinking agent may be effectively added at any stage of the process, the effect of the addition can be rendered more remarkable by supplying heat energy in the cource of the drying, whereby the physical strength of the catalysts, that is, immobilized enzyme compositions is greatly enhanced, as well as the stability in the enzymatic activity can be improved to produce catalysts of an industrial excellency.

The advantageous features of the excellent immobilized enzyme compositions (catalysts) obtained by the process according to this invention are summarized as follows:

Since the compositions substantially consist of enzymes, highest enzymatic activity can be provided and, in addition, pelletized catalysts of any desired shape and size can be produced by mechanical molding by suitably controlling the molding conditions.

This enables to maintain the reaction at a sufficiently high rate, supplying a material at a high feed rate into a reactor of an industrial scale packed with the enzyme according to the invention. Moreover, since the catalyst is chemically crosslinked and mechanically molded, it possesses a high physical strength and provides an excellent penetration to the liquid passing through the reactor to reduce the pressure losses and to ensure stabilized operation.

In addition, since the mechanical molding and chemical crosslinking improve the chemical stability, there can be obtained various other advantages which were not present in the conventional processes, e.g. less deactivation of the enzyme even during the continuous long use and less effects of the impurities.

Further, the process of this invention is effective not only for the immobilization of an individual enzyme and/or enzyme-containing microorganic cells but also for the immobilization for a plurality of enzyme and/or enzyme-containing cells in combination and therefore provides a wide variety of applications.

DETAILED DESCRIPTION OF THE INVENTION (1) Enzymes and Microorganisms

The enzymes and/or enzyme-containing microorganic cells used in this invention include, for example, enzyme (A) or enzyme-containing microorganic cells (C) individually; enzyme (A)+enzyme (B); enzyme (A)+enzyme-containing microorganic cells (C)+enzyme-containing microorganic cells (D).

Representatives of the enzymes usable in the process of this invention include; glucose isomerase, lactase, aminoacylase, penicilline amidase, glucose oxidase, urease, phenoloxidase, catalase, invertase, alcohol dehydrogenase, lysozyme, steroid dehydrogenase, steroid hydroxylase, lactate dehydrogenase, amino acid oxidase, tyrosinase, ribonuclease, lipase, cellulase, $\alpha$-amylase, glucoamylase, mellibiase, asparaginase, $\beta$-amylase, maltase, cyclodextranase and the like, and the enzymes above may be used as contained in microorganic cells.

(2) Carriers

The anion-exchange resin containing a quaternary pyridine ring in the molecule used as carriers in this invention means a water insoluble but highly hydrophilic reactive high polymer produced by reacting a reagent capable of quaternizing the nitrogen atom in the pyridine ring in a copolymer which is produced by the copolymerization of vinylpyridine or its derivatives with one or more of the monomers capable of copolymerizing therewith and selected from the groups of aromatic vinyl compounds, ethylenically unsaturated compounds and unsaturated diene series compounds.

The concreate anion-exchange resin suitably used in this invention includes those having a quaternary pyridine ring in the molecule and obtained by reacting a quaternizing reagent such as alkyl halide or alkyl dihalide with vinylpyridine-styrene-divinylbenzene copolymer, vinylpyridine-methylmethacrylate-divinylbenzene copolymer, vinylpyridine-polyethyleneglycol-dimethacrylate copolymer, vinylpyridine-styrene block copolymer, vinylpyridine-methylmethacrylate block copolymer and the like.

(3) Crosslinking Agents

The preferred polyfunctional crosslinking agents usable in this invention are those compounds capable of reacting with functional reactive groups such as quaternary pyridine group, and pyridine group in the carrier, and hydroxyl, carboxyl, phenol, amino, mercapto groups or the likes in the enzymes and/or microorganic cells and they, desirably, include aldehydes, acid anhydrides, epoxides, halides, isocyanates and the likes. More specifically, they include dialdehyde starch, glutaraldehyde, urea-formaldehyde compound, succinic anhydride, maleic anhydride copolymer, epichlorohydrin, epoxy resin, s-chlorotriazine, amino dichlorotriazine, toluene diisocyanate, dichlorobutene, Woods ward reagent and the like. In the above compounds, dialdehyde starch is particularly effective among others to this invention.

Since most of the crosslinking agents generally react with the reactive groups in the enzymes to reduce the enzymatic activity, although they can improve the physical strength of the enzymes, a sufficient care must be taken for the employment of a high reactive crosslinking agent in the production of immobilized enzymes. However, the use of dialdehyde starch in combination with carriers containing a quaternary pyridine ring can improve the catalyst strength with no substantial reduction in the enzymatic activity.

PRODUCTION OF IMMOBILIZED ENZYME CATALYSTS (1) Coagulation reaction between enzymes and/or enzyme-containing microorganic cells and a carriers The reaction between the enzymes and/or enzyme-containing micoorganic cells and the carriers is, desirably, effected in a liquid phase reaction wherein an aqueous dispersion of the carriers is added to and mixed with the enzyme and/or enzyme-containing microorganic cells which has been dissolved or dispersed in water at each of their optimum pH range, to have them immobilized through coagulation.

A coagulated phase reaction is further desired wherein the aqueous dispersion of the carriers is added to and mixed with the enzyme and/or enzyme-containing microorganic cells in a dried state to immobilize them through coagulation.

Preferred carriers used herein are finely divided powder of less than 0.1 mm particle diameter which is desirably produced by powderizing in the course of the production step for the carriers or powderizing the resulted carriers in a grinding machine or a ball mill. Since the carriers are highly acidic, it is desired to use an aqueous dispersion of the carriers adjusted to a pH range between 5.0-9.0.

An appropriate addition ratio between the enzymes and/or microorganic cells and the carriers is 1:0.005-1:0.5 and, more preferably, 1:0.05-1:0.2 in each of their dried weights. Outside of the above range, the immobilizing reaction through coagulation may be insufficient or excess carriers may cause undesired effects on the enzymatic activity.

The immobilizing reaction through coagulation above described is, desirably, effected at a temperature between 0°-30° C. considering the degradation of the enzymes or the like.

The immobilized enzymes and/or immobilized microorganic cells are molded in a molding machine in a wet condition containing a certain amount of water. It is preferred to adjust the water contents in the wet immobilized products to between 25-80% which is attainable by the control of mechanical conditions for a centrifugal separator or a filter press in the case of the immobilizing reaction through coagularion in a liquid phase, or by the mere addition of water in a desired amount prior to the molding in the case of the reaction effected in a coagulated phase.

(2) Molding of wet immobilized products

Molding of the wet immobilized products is effected in a molding machine corresponding to a desired final shape of the catalyst.

The catalyst desirably has a final shape of ellipsoid or rounded head and a thickness or diameter between about $1\mu$–10 mm, preferably, $100\mu$–2 mm considering the well balanced combination between the initial enzymatic activity and the penetration to liquid. In a preferred molding method employed in this invention, the wet immobilized products are molded in an extruder having a 0.1 mm-2 mm screen. In the extrusion, the extruder used requires no special structure and a conventional type of extruder can suffice the above purpose.

For further pelletizing the molded products, a rotary pelleting machine is advantageously used. By the optimum selection of the revolutional number and time, catalyst can be formed into a shape and a size suited to this invention. It is also desired that the molding operation is effected in a shorter time and at a lower temperature (0°-25° C.) as much as possible to prevent the degradation of the catalyst.

It is effective in the extrusion molding, for the improvement in the extrusion property, stabilization of the shape and size of the molded pellets, as well as for giving porosity to the catalyst, to add various fillers such as inorganic substance, for example, diatomaceous earth, silica; and aqueous dispersion of starch, dextrin, sodium alginate, carboxymethylcellulose, polyvinylalcohol, cellulose acetate, ethylene-vinylacetate copolymer, sodium polyacrylate or the like.

(3) Drying of the molded products

The molded products produced as described above should be dried rapidly. While it is desired to effect drying by blowing air at 40°-80° C. for 15 minutes-20 hours, the drying can be effected either with a shelf type drier in a stationary state or with a fluidized bed drier in a fluid state. Drying at higher temperature for a long time will result a remarkable reduction in the enzymatic activity and lower temperature drying takes a longer time to result the degradation in the enzyme and/or micoorganic cells.

(4) Crosslinking for the catalyst

The crosslinking reaction for the enzymes and/or enzyme-containing microorganic cells can be effected at any stage in the production process of this invention. In a preferred embodiment, a crosslinking agent is added in a solution containing the crosslinking agent to any desired density appropriate to the property of the agent at the time the coagulating immobilization is taken place where the enzymes and/or enzyme-containing microorganic cells are reacted with the carriers.

Where dialdehyde starch is used as the crosslinking agent, it is added, preferably, as a 1–20% aqueous solution so as to provide 0.1–10% by weight of dialdehyde starch based on the solid contents of the enzyme and/or enzyme-containing microorganic cells.

In a alternative preferred embodiment, the crosslinker solution is added at the same time when the wet immobilized products after the coagulating immobilization are molded in a molding machine.

In another preferred embodiment, the wet products molded in a molding machine are contacted with the solution of the crosslinking agent.

In a further preferred embodiment, the solution of the crosslinking agent is contacted to the molded products after they have been dried.

Where dialdehyde starch is used as the crosslinking agent, it is preferred to contact the molded products in a dried state with an 0.5–20% aqueous solution of the dialdehyde starch for five minutes–five hours. In the above case, strength and stability of the catalysts can further be improved by drying them in the manner described after the completion of the crosslinking reaction.

Solvent for the crosslinking agent should be selected depending on the solubility of the agent and where a water insoluble crosslinking agent is used it is dissolved into a mixed solution of a non-aqueous organic solvent and water to prepare a solution. Such a mixed solvent of the non-aqueous organic solvent and water is used also for a water soluble crosslinking agent, if it is highly reactive, to moderate the reactivity thereof because it may possibly attack the active groups in the enzymes to cause deactivation.

Preferred examples for the non-aqueous organic solvents include acetone, methanol, ethanol, propanol, isopropanol, tetrahydrofuran, dioxane, dimethylformamide, dimethylsulfoxide, glycerine, polyethyleneglycol and the like.

The amount and the concentration of the crosslinking agent used for the enzymes and/or enzyme-containing microorganic cells have no particular limits since they are varied depending on the effects of the solubility and reactivity of the crosslinking agent, as well as the activity and strength desired for the catalyst.

pH range for the solution of the crosslinking agent should be determined based on the enzymatic activity and the crosslinking effect and adjusted suitably to between 4.0–9.0, more preferably, near to a neutral point.

It is desired to effect the crosslinking reaction at a lower temperature and in a shorter time as much as possible in order to minimize the degradation in the enzymes.

Since the immobilized enzyme catalysts thus obtained consist essentially of the enzymes and/or enzyme-containing microorganic cells and a minor amount of carriers, highest enzymatic activity per unit weight of the catalysts can be realized and, in addition, since the catalysts have a dense and solidified structure by the mechanical molding and chemical crosslinking reaction, the penetration to the liquid is excellent and the pressure loss caused by the degradation of the catalyst is not observed at all through the reaction.

Being solidified in structure and crosslinked chemically, the enzymes have an improved stability, suffer from least degradation in the enzymatic activities even in the continuous use for a long time and thus provide catalysts of excellent industrial advantages.

This invention will now be described in detail by way of examples 1 through 11.

EXAMPLE 1

(1) Preparation of immobilized catalyst

A monomer mixture consisting of 48 mol% styrene, 50 mol% 2-vinylpyridine, 2 mol% divinylbenzene was added to water, which contains 5% sulfate salt of polyoxyethylene alkylphenolether (Nissantrax K, as commercial name) as an emulsifier in a monomer to water ratio of 1:½ by volume, emulsified therein and, thereafter, emulsion polymerized at 60° C. using potassium persulfate as a catalyst.

10 hours after the reaction, an excess amount of acetone was added to the reaction solution to precipitate the resulted polymer in powderized state, and the precipitants were washed with warm water for several times and then dried. The polymerization degree was 95%.

The copolymer thus obtained was quaternized in a pressurized gas phase at 80° C. using methylbromide as a quaternizing agent. 50 g of the quaternized styrene - 2-vinylpyridine-divinylbenzene random copolymer (anion-exchange capacity of 3.2 meq/g) was dispersed in 250 ml water into a suspension and adjusted to pH 7.0 by using 0.1 N NaOH.

Then, an aqueous dispersion of commercially available microorganic cells having glucose isomerase activity produced from Streptomyces species (enzymatic activity of 1600 GIU/g; about 40% solid contents) was sonificated and, thereafter, the supernatant liquid was condensed and then freeze-dried. 50 cc of the carrier dispersion prepared as above was added to 100 g of the glucose insomerase (15000 GIU/g of activity) and well compounded to prepare coagulated immobilized products.

50 ml of 5% aqueous solution of dialdehyde starch prepared by treating starch with periodic acid (containing 10% of sodium sulfite to solid content: pH 6.0) was then added to the above coagulated immobilized products and well compounded at a room temperature.

The compounded products were subjected to extrusion molding at an ambient temperature using a single screw front surface extruder having a 1.0 mm φ screen. The extrudate strip of 2–10 cm width was cut to a 1 mm length and then dried in a fluidized bed drier at 60° C. for one hour. The immobilized enzyme catalyst thus obtained possessed glucose isomerase activity of 4800 GIU/g. (Remark 1)

(2) Continuous enzyme reaction 100 g of the immobilized enzymes prepared as described in (1) above, was placed in a beaker containing 1 liter of distilled water and swelled for about one hour. They were then packed in a jacketed glass column of 2.5 cm diameter and 80 cm height kept at 60° C. and, immediately thereafter, 59% by weight of an aqueous solution of glucose (pH: 8.0, and containing $5\times 10^{-3}$ M/l $MgSO_4.7H_2O$) was supplied continuously from above the column at a flow rate of 1500 ml/Hr. to initiate the reaction.

Pressure gages were set at the upper and the lower portions of the column so as to measure the pressure difference. The reacted solution was taken out from the lower portion of the column and the isomerization rate was given by the determination of the resulted amounts of fructose by using a polariscope. The results are shown in table 1.

Table 1

| Days | Flow rate (l/Hr) | Yield of fructose (% - solid content) | Pressure loss (kg/cm²) |
| --- | --- | --- | --- |
| 2 | 1500 | 44.5 | 0.03 |
| 5 | 1500 | 47.3 | 0.03 |
| 10 | 1500 | 45.4 | 0.03 |
| 20 | 1500 | 46.1 | 0.03 |
| 30 | 1500 | 43.0 | 0.03 |
| 40 | 1500 | 42.2 | 0.03 |
| 50 | 1500 | 41.0 | 0.03 |

(REMARK 1)

The enzymatic activity of glucose isomerase was measured on the basis of Takasaki's method (reported in Agricultural Biological Chemistry vol. 30, 1248 pp (1966)) wherein activity units were indicated by assuming the unity, 1 GIU/g, to represent production of 1 mg of fructose from 1 g of a given enzymatic composition under the reaction conditions of 70° C. for 10 minutes.

EXAMPLE 2

(1) Preparation of immobilized catalyst

To 1000 g of the same commercially available microorganic cells possessed of glucose isomerase activity (1600 GIU/g; about 40% solid content) as used in (1) in example 1 above, was flown down 250 ml of an aqueous solution containing 50 g of the same quaternized random copolymer of styrene - 2-vinylpyridine-divinylbenzene (pH 7.0) as prepared in example 1 while compounding in a kneader. After compounding for about 15 minutes at a room temperature (25° C.), 25 ml of a 10% aqueous solution of dialdehyde starch (pH 6.0) used in example 1 was added and compounding was effected for a further 15 minutes.

The wet immobilized microorganic cells were then subjected to extrusion molding at an ambient temperature in a twin screw horizontal extruder having a 0.5 mm $\phi$ screen and the extrudates were pelletized in a rotary pelletizer under the operation conditions of 750 rpm and 30 seconds/batch. The resultant pellets were dried by a fluidized bed drier for one hour at 60° C. The catalyst had an activity of 1030 GIU/g.

(2) Continuous enzyme reaction

Uing 100 g of the catalyst prepared in (1) above, glucose isomerization was conducted by the same method as in example 1 - (2). The results are shown in table 2.

Also in this reaction, the resulted products were quite colorless and of a high quality. In addition, since the pressure loss is extremely low, operation can be performed with safety.

Table 2

| Days | Flow rate (ml/hr.) | Yield of fructose (% to solid content) |
| --- | --- | --- |
| 2 | 480 | 41.5 |

Table 2-continued

| Days | Flow rate (ml/hr.) | Yield of fructose (% to solid content) |
| --- | --- | --- |
| 5 | 500 | 42.5 |
| 10 | 470 | 42.7 |
| 20 | 470 | 40.5 |
| 30 | 470 | 38.3 |
| 40 | 470 | 37.0 |
| 50 | 470 | 36.0 |

EXAMPLE 3

(1) Preparation of immobilized catalyst 50 g of quaternized random copolymer of styrene - 2-vinylpyridine - divinylbenzene as prepared in example 1 - (1) was dispersed to 5 l of water in suspension and pH was adjusted to 7.0 with 0.1 N NaOH.

Then, 1000 g of the same microorganic cells possessed of glucose isomerase activity as used in example 1 (1) was suspended in 10 l of water, to which the whole parts of the copolymer dispersion described above were added while stirring at a room temperature (20°-25° C.). After a 30 minute agitation, they were dewatered in a centrifugal separator to obtain immobilized wet microorganic cells. The yield was 1250 g (68% water contents).

200 ml of a 2% aqueous solution of carboxymethylcellulose (commercially available as food additives) was added thereto and thoroughly compounded to a water content of about 72.5%.

The immobilized wet microorganic cells thus produced were then subjected to extrusion molding in a twin screw horizontal extruder having a 0.8 mm $\phi$ screen. The extrudates were pelletized in a pelletizer under the operation conditions of 500 rpm and 60 seconds/batch and the resulted wet pelletized products were dried for 20 hours using a blowing drier maintained at 50° C.

Then, 100 g dried pellets were added to 100 ml of a 2% aqueous solution (pH 6.0) at 5° C. of the same dialdehyde starch as used in example 1 - (1) to react for about 30 minutes. After the reaction, solid contents were filtered out, washed with pure water and then dried for one hour at 60° C. using a fluidized bed drier. The catalyst obtained had 980 GIU/g of activity.

(2) Continuous enzyme reaction

Using 100 g of the catalyst prepared as in (1) above, glucose isomerization was conducted by the same method as in example 1 - (2). The reaction was initiated at a reactant flow rate of 450 ml/hr. in which the yield of fructose (% to solid content) was 43.5% at an initial stage and 40.3% after 30 days. Neither the pressure loss nor the collapsion in the catalyst was observed at all in the course of the reaction.

EXAMPLE 4

(1) Preparation of immobilized catalyst

A quaternized random copolymer of MMA - 2-vinylpyridine-divinylbenzene (anion-exchange capacity of 3.0 meq/g) was produced in the same way as in the production for the carriers described in the example 1 - (1) excepting the use of methylmethacrylate (MMA) in place of styrene.

Then, while kneading 1000 g of the same commercially available microorganic cells possessed of glucose isomerase activity as in the example 1 - (1) in a kneader, 250 ml of an aqueous dispersion (pH 7.0) containing 50 g of the above carriers was added thereto and the kneading was effected for a further about 15 minutes at a room temperature (25° C.).

Then, the immobilized wet microorganic cells thus obtained were molded and dried in the same way as in the example 3 - (1) to obtain dried pelletized products. 100 g of the pellets were then immersed into 500 ml of a mixed solution of water and acetone (pH 7.0, water-/acetone ratio=1:4 by volume) containing 5% (w/v) glutaraldehyde and reacted for 30 minutes at 5° C. After filtration, the filtered products where washed with acetone for several times and dried by blowing for two hours at 60° C. The catalyst had 730 GIU/g activity.

(2) Continuous enzyme reaction

Using 100 g of the catalyst prepared as in (1) above, glucose isomerization was effected in the quite same manner as in the example 1 - (2).

The reaction was initiated with a reactant flow rate of 380 ml/hr., in which the yields for fructose (% to solid content) was 45.3% at an initial stage, 42.5% after 30 days and 41% after 60 days. Neither the pressure loss nor the collapsion in the catalyst was observed at all throughout the reaction.

EXAMPLE 5

(1) Preparation of immobilized catalyst 50 g of the quaternized random copolymer of MMA - 2-vinylpyridine - divinylbenzene as used in the example 4 - (1) was dispersed in 250 ml of water in suspension and pH was adjusted to 7.0.

Then, 100 ml dispersion of the above carriers was added to and well compounded with 100 g of commercially available glucoamylase (activity unit, 30000 U/g) to prepare coagulated immobilized products.

The immobilized products were then subjected to extrusion molding in a single screw front extruder having a 1.0 mm φ screen at an ambient temperature. The resultant extrudate strip was cut to about 1 mm length and, thereafter, dried at 60° C. for one hour in a fluidized bed drier. Then, 100 g of the pelletized products were treated with glutaraldehyde and dried in the same conditions as in the example 4 - (1). The catalyst had a 2500 U/g (refer to remark 2) of activity.

(2) Continuous enzyme reaction 100 g of the immobilized enzyme catalyst prepared as in (1) above was swelled in water for about one hour and then packed into a jacketed glass column of 2.5 cm diameter and 80 cm height kept at 40° C. Immediately after, 35% solution of liquified potato starch (pH 4.8 DE 13) was continuously supplied from the top of the column at a flow rate of 1000 ml/hr. to initiate the reaction. The reaction solution was sampled out at a certain interval of time from the bottom of the column and the yields of glucose were determined according to the glucostat method. The results are shown in table 3.

Table 3

| Days | Flow rate (ml/hr.) | Yield of glucose (% to solid content) |
|---|---|---|
| 2 | 1000 | 97.0 |
| 5 | 1000 | 95.2 |
| 10 | 1000 | 94.6 |
| 15 | 1000 | 94.0 |
| 20 | 1000 | 93.6 |
| 30 | 1000 | 92.8 |
| 40 | 800 | 95.0 |
| 50 | 800 | 94.3 |

(REMARKS 2)

Glucoamylase activity: Yield of the reducing sugar was determined using a 1.2% solution of soluble starch (pH 4.5) as a basic reactant and according to the Somogyi-Nelson method (experimental methods in biochemistry, "Method for determination of reducing sugar" p10 published by Tokyo University Publishing Association). Activity units were indicated by assuming the unity, 1 unit/g, to represent liberation of reducing power corresponding to 100 μg of glucose for one minute from 1 g of the enzyme pellets.

EXAMPLE 6

(1) Preparation of immobilized catalyst 100 g of commercially available glucoamylase (activity unit of 30000 U/g) was dissolved into 100 ml of water. Then, 200 ml of a 10% acetone solution of maleic anhydride-vinylacetate copolymer (in 1:1 ratio) was gradually added to the above solution under agitation and pH was adjusted to 7.0–8.0 with 1/10 N NaOH. The reaction was conducted at 5°–10° C. After entire portion of the copolymer had been added, agitation was continued for a further 10 minutes and then freeze-drying was effected to obtain succinic glucoamylase.

Then, 50 ml of the same dispersion as in the example 5 - (1) is added to and well compounded with the above enzyme and further mixed thoroughly with 50 ml of an aqueous solution of the same dialdehyde starch as in the example 1 - (1) at a room temperature (25° C.). The wet immobilized products were then molded and dried in the same methods as in the example 4 - (1) to prepare the catalyst. The catalyst had a 2800 U/g of activity.

(2) Continuous enzyme reaction

Using 100 g of the immobilized enzyme catalyst prepared in (1) above, a continuous saccharification of starch was effected in the same manner and under the same conditions as in the example 5 - (2). The reaction was conducted for 50 days while setting the flow rate of the basic reactant to 1000 ml/hr. and, as the result, the yield for the glucose resulted was more than 94.0%.

EXAMPLE 7

(1) Preparation of immobilized catalyst

Aminoamylase-incorporating microorganic cells produced by a deep culture of Aspergillus oryzae were subjected to spray-drying. 100 g of the dried cells were used for the immobilization and catalyst formation quite in the same way as in the example 1 - (1) to produce immobilized enzyme catalyst.

(2) Continuous enzyme reaction 100 g of the above catalyst was swelled in water for about one hour and then packed into a jacketed glass column of 2.5 cm diameter and 80 cm height kept at 50° C. N-acetyl-DL-methionine solution (0.2 mol, pH 7.0 added with $5.0 \times 10^{-4}$ mol $CoCl_2$) was flown down from the top of the column at a flow rate of 1000 ml/hr. The reaction solution flown out from the bottom of the column was sampled on every certain interval of time to determin the amount of L-methionine by way of ninhydrine colorimetry. The results are shown in table 4.

Table 4

| Days | Flow rate (ml/hr.) | Yield of L-methionine (% to N-acetyl-L-methionine) |
|---|---|---|
| 2 | 1000 | 100.0 |
| 5 | 1000 | 100.0 |
| 10 | 1000 | 100.0 |

Table 4-continued

| Days | Flow rate (ml/hr.) | Yield of L-methionine (% to N-acetyl-L-methionine) |
| --- | --- | --- |
| 15 | 1000 | 99.6 |
| 20 | 1000 | 99.4 |
| 30 | 1000 | 99.0 |
| 40 | 970 | 100.0 |
| 50 | 970 | 99.5 |
| 60 | 950 | 100.0 |

EXAMPLE 8

(1) Preparation of immobilized catalyst 100 g of commercially available aminoamylase (activity unit 25000 U/g) was used to produce immobilized aminoamylase catalyst quite in the same methods and at the same conditions as in the example 5-(1).

(2) Continuous enzyme reaction

Using 100 g of the above catalyst, continuous production of L-methionine was effected in the same methods and at the same conditions as in the example 7-(2). The reaction was conducted continuously for 60 days while setting the flow rate of the basic reactant to 4 l/hr. and, as the result, the yield for the L-methionine (to N-acetyl-D-methionine) was more than 99.5%.

EXAMPLE 9

(1) Preparation of immobilized catalyst 100 g of commercially available glucoamylase (activity unit 30000 U/g) was dissolved in 1000 ml of pure water. Then, 200 ml of a 10% acetone solution of maleic anhydride-vinylacetate copolymer (in 1:1 ratio) was gradually added to the above solution while stirring and the solution was adjusted to pH 7.0-8.0 with 1/10N NaOH. The reaction was effected at 5-10° C. After the completion of additio, agitation was continuted for a further 10 minutes and then freeze-drying was effected to obtain succinic glucoamylase.

Then, 50 ml of the same carrier dispersion as in the example 8-(1) was added to and sufficiently mixed with 100g of the above enzyme and, thereafter, 50 ml of an aqueous solution of the same dialdehyde starch as in the example 4-(1) was further added and thoroughly compounded therewith at a room temperature (25° C.).

The immobilized wet products were dried and formed into catalysts in the same ways as in the example 4-(1). The catalyst had a 2800 U/g of activity.

(2) Continuous enzyme reaction

Using 100 g of the immobilized enzyme catalyst as prepared in (1) above, continuous saccharification of starch was effected in the same method and at the same conditions as in the example 8-(2). The reaction was effected continuously for 50 days while setting the flow rate of basic reactant to 1000 ml/hr., as the result, giving a glucose yield of more than 94.0%.

EXAMPLE 10

(1) Preparation of immobilized catalyst

Aminoamylase-containing microorganic cells produced by the deep culture of Aspergillus oryzae were spray-dried. 100 g of the dried cells were used for the immobilization and formation of catalyst to produce immobilized enzyme catalyst quite in the same way as in the example 4-(1).

100 g of the above catalyst was swelled in water for about one hour and packed into a jacketed glass column having 2.5 cm diameter and 80 cm height and kept at 50° C. Solution of N-acetyl-DL-methionine (0.2 mol, pH 7.0, added with $5.0 \times 10^{-4}$ mol $CoCl_2$) was continuously flown down from the top of the column at a flow rate of 1000 ml/hr. The reaction solution flown out of the bottom of the column was sampled on every certain interval of time and the amount of the L-methionine produced was determined by way of ninhydrine colorimetry. The results are shown in table 6.

Table 6

| Days | Flow rate (ml/hr.) | Yield for L-methionine (% to N-acetyl-L-methionine) |
| --- | --- | --- |
| 2 | 1000 | 100.0 |
| 5 | 1000 | 100.0 |
| 10 | 1000 | 100.0 |
| 15 | 1000 | 99.6 |
| 20 | 1000 | 99.4 |
| 30 | 1000 | 99.0 |
| 40 | 970 | 100.0 |
| 50 | 970 | 99.5 |
| 60 | 950 | 100.0 |

EXAMPLE 11

(1) Preparation of immobilized catalyst 100 g of commercially available aminoamylase (activity unit 25000 U/g) was used in the same methods and at the same conditions as in the example 8-(1) to produce immobilized aminoamylase catalyst.

(2) Continuous enzyme reaction

Using 100 g of the above catalyst, continuous production for L-methionine was effected in the same methods and at the same conditions as in the example 10-(2). As the result of the continuous reaction for 60 days setting the flow rate of the basic reactant to 4 l/hr., more than 99.5% of yield was obtained for L-methionine (to N-acetyl-D-methionine).

What is claimed is:

1. A process for producing an immobilized enzyme composition which comprises the steps of reacting enzyme and/or enzyme containing microorganic cells with a cross-linking agent and an anionic exchange high molecular substance containing a quaternary pyridine ring in the molecule at a weight ratio of the enzyme and/or enzyme containing microorganic cells to the anionic exchange high molecular substance of between 1:0.005 and 1:0.05, in an aqueous dispersion having a pH range of from about 5 to 9, at a temperature from about 0° C. to about 30° C, adjusting the water contents of the resulting reaction products to from about 25 to about 80 wt.%, subjecting to extrusion molding the adjusted reaction products with an extruder at a temperature from about 0° C. to 25° C., thereby obtaining an extrudate, pelletizing said extrudate, and then drying the pellets at a temperature from about 40° C. to 80° C. for about 15 minutes to 20 hours.

2. The process of claim 1 wherein the enzyme-containing microorganic cells are selected from the group consisting of cells containing glucose isomerase, glucoamylase and aminoacylase.

3. The process of claim 1 wherein said enzyme is selected from the group consisting of glucose isomerase, glucoamylase and aminoacylase.

4. The process of claim 1, wherein the extruder is a twin screw horizontal type extruder.

5. A process for producing an immobilized enzyme composition which comprises the steps of reacting enzyme and/or enzyme containing microorganic cells with an anionic exchange high molecular substance containing a quaternary pyridine ring in the molecule at a weight ratio of the enzyme and/or enzyme containing microorganic cells to the anionic exchange high molecular substance of between 1:0.005 and 1:0.5, in an aqueous dispersion having a pH range of from about 5 to 9, at a temperature from about 0° C. to about 30° C., adjusting the water content of the resulting reaction products to from about 25 to about 80 wt.%, subjecting to extrusion molding the adjusted reaction products in the presence of a cross-linking agent with an extruder at a temperature of from about 0° C. to 25° C., thereby obtaining an extrudate, pelletizing said extrudate, and then drying the resulted pellets at a temperature from about 40° C. to 80° C. for about 15 minutes to 20 hours.

6. A process for producing an immobilized enzyme composition which comprises the steps of reacting enzyme and/or enzyme containing microorganic cells with an anionic exchange high molecular substance containing a quaternary pyridine ring in the molecule at a weight ratio of the enzyme and/or enzyme containing microorganic cells to the anionic exchange high molecular substance of between 1:0.005 and 1:0.5, in an aqueous dispersion having a pH range of from about 5 to 9, at a temperature from about 0° C. to about 30° C., adjusting the water content of the resulting reaction products to from about 25 to about 80 wt.%, subjecting to extrusion molding said adjusted products with an extruder at a temperature from about 0° C. to 25° C., thereby obtaining an extrudate, contacting said extrudate with a solution of a cross-linking agent, pelletizing the resulting extrudate, and then drying the pellets at a temperature from about 40° C. to 80° C. for about 15 minutes to 20 hours.

7. A process for producing an immobilized enzyme composition which comprises the steps of reacting enzyme and/or enzyme containing microorganic cells with an anionic exchange high molecular substance containing a quaternary ring in the molecule at a weight ratio of the enzyme and/or enzyme containing microorganic cells to the anionic exchange high molecular substance of between 1:0.005 and 1:0.5, in an aqueous dispersion having a pH range of from about 5 to 9, at a temperature from about 0° C. to about 30° C., adjusting the water contents of the resulting reaction products to from about 25 to about 80 wt.%, subjecting to extrusion molding the adjusted reaction products with an extruder at a temperature from about 0° C. to 25° C., thereby obtaining an extrudate, pellitizing said extrudate, and then drying the pellets at a temperature from about 40° C. to 80° C. for about 15 minutes to 20 hours, and contacting said dried pellets with a solution of a cross-linking agent.

8. The process of any of claims 1, 5, 6 or 7 wherein said extruder has a screen of 0.1 to 2.0 mm.

9. The process any of claims 1, 5, 6 or 7, wherein the crosslinking agent is dialdehyde starch.

10. The process any of claims 1, 5, 6 or 7, wherein the crosslinking agent is glutaraldehyde.

11. The process any of claims 1, 5, 6 or 7, wherein the crosslinking agent is selected from the group consisting of condensation products of ureaformaldehyde, succinic anhydride, maleic anhydride copolymer, epichlorohydrin, epoxy resin, cyanuric acid chloride, aminodichlorotriazine, toluene diisocyanate, dichlorobutene and Woodward's reagent.

12. The process any of claims 1, 5, 6 or 7, wherein the weight ratio of the enzyme and/or enzyme containing microorganic cells to the anion exchange high molecular substance is in the range of from 1:0.05 to 1:0.2.

13. The product of the process any of claims 1, 5, 6 or 7.

* * * * *